United States Patent [19]

Oda

[11] Patent Number: 4,871,266
[45] Date of Patent: Oct. 3, 1989

[54] SLIDE ASSEMBLIES

[75] Inventor: Isao Oda, Nagoya, Japan

[73] Assignee: NGK Insulators, Ltd., Nagoya, Japan

[21] Appl. No.: 135,276

[22] Filed: Dec. 21, 1987

[30] Foreign Application Priority Data

Jun. 24, 1987 [JP] Japan .................... 62-155400
Oct. 19, 1987 [JP] Japan .................... 62-261770

[51] Int. Cl.$^4$ .................... F16C 33/62; F16C 29/02
[52] U.S. Cl. .................... 384/42; 384/14; 384/463; 384/492; 384/907
[58] Field of Search .................... 384/7, 13, 14, 23, 26, 384/28, 42, 50, 276, 297, 322, 463, 492, 625, 907, 907.1, 912, 913

[56] References Cited

U.S. PATENT DOCUMENTS

| 2,901,380 | 8/1959 | Crump | 384/322 X |
| 3,097,897 | 7/1963 | Taylor | 384/492 |
| 3,376,082 | 4/1968 | Soder | 384/42 |
| 3,711,171 | 1/1973 | Orkin et al. | 384/297 |
| 4,664,595 | 5/1987 | Tsuji et al. | 384/907 X |

FOREIGN PATENT DOCUMENTS

| 1297869 | 11/1972 | United Kingdom . |
| 1343930 | 1/1974 | United Kingdom . |
| 2079869 | 1/1982 | United Kingdom | 384/322 |

Primary Examiner—Thomas R. Hannon
Attorney, Agent, or Firm—Arnold, White & Durkee

[57] ABSTRACT

Slide assemblies, which each include a metallic member and a ceramic member to slide with the metallic member. The metallic member has a sliding surface coated with a mixture consisting essentially of a solid lubricant and a binder. The mixture of the solid lubricant and the binder is a combination selected from the group consisting of $LiF+MoO_3$, $PbO+Cu$, $MoS_2+Cu$, $LiF+Ni$—Cr—Mo—Si, and $LiF+Co$—Mo—Cr—Si. Silicon nitride, sialon, mullite, partially stabilized zirconia, or silicon carbide is preferably used as the ceramic member. The slide assemblies exhibit excellent high frictional resistance and wearing resistance even in dry condition at high temperatures.

13 Claims, 3 Drawing Sheets

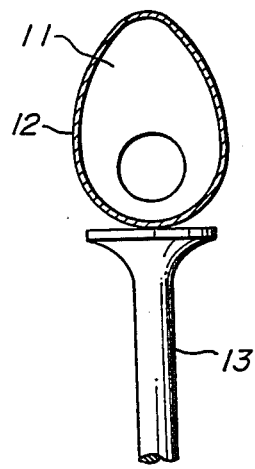
FIG._2
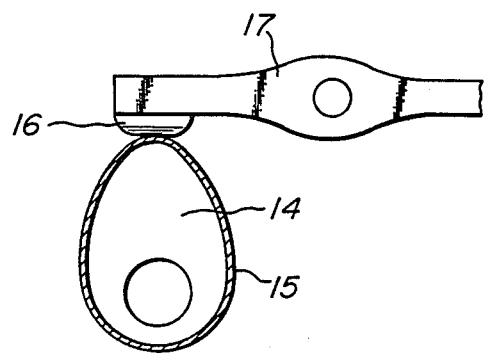
FIG._3
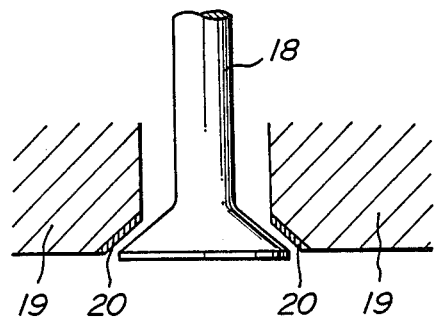
FIG._4
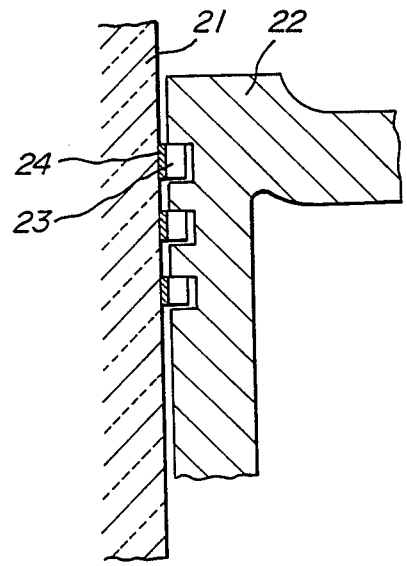
FIG._5

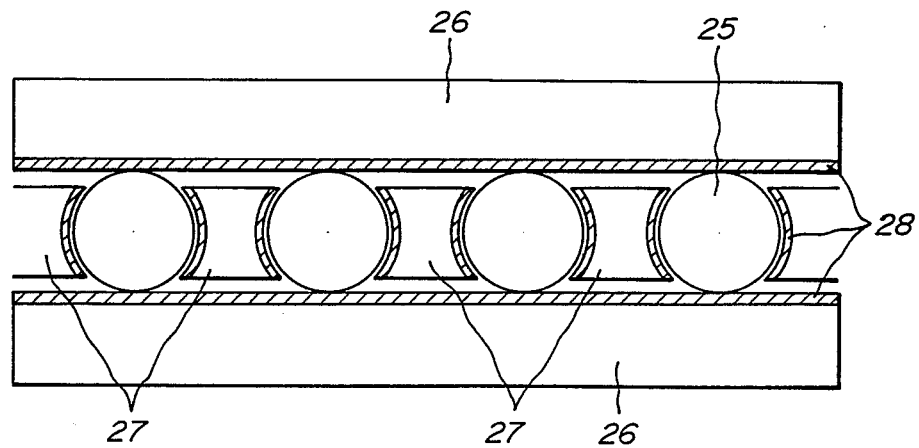
FIG_6

SLIDE ASSEMBLIES

BACKGROUND OF THE INVENTION (1) Field of the Invention

The present invention relates to slide assemblies using ceramic members.

(2) Related Art Statement

Since slide members, particularly, slide members used in engines and the like are heated at high temperatures and must withstand friction under high speed rotation, metallic materials which withstand high temperatures, for instance, heat resisting alloys, and the like, have formerly been used by employing a liquid lubricant such as oil as an intermediate.

However, use conditions required for the slide members have been getting severer year by year, and there is a demand for operating such slide members without using a liquid lubricant. Metallic materials have a defect that they can not withstand use temperatures or friction or they must be replaced after a short cycle.

Under the circumstances, it has been considered that ceramic materials are used as slide members.

While ceramic materials withstand high temperatures and have high wear resistance, they are unfavorably brittle. However, all ceramic materials cannot be used for this purpose. Coefficients of friction between ceramic materials and metallic materials in a high temperature dry atmosphere are generally in a range of from about 0.5 to about 0.6, which is considerably higher as compared with a coefficient of friction of 0.1 to 0.2 required for slide members used in engines, and the like.

In order to eliminate the above-mentioned problem, NGK Insulators, Ltd. discloses in Japanese patent application Laid-open No. 62-13,820 a slide assembly comprising a ceramic member and a metallic member having a slide surface coated with a mixture of LiF and Cu.

However, although the slide assembly disclosed in Japanese patent application Laid-open No. 62-13,820 can attain excellent sliding performance, its coefficient of friction is around 0.4. Further, a wear amount of a mating member is large during sliding. Thus, such a slide assembly does not afford sufficient sliding performance as in engines or the like.

SUMMARY OF THE INVENTION

It is an object of the present invention to eliminate the above-mentioned problems, and to provide a slide assembly which is suitable as slide members for use in engines or the like, said slide assembly having a low coefficient of friction and a smaller wear amount.

The slide assembly according to the present invention comprises a metallic member and a ceramic member to slide relative to each other, and is characterized in that a mixture consisting essentially of a solid lubricant and a binder is coated onto a sliding surface of the metallic member and the mixture of the solid lubricant and the binder is a combination selected from the group consisting of $LiF+MoO_3$, $PbO+Cu$, $MoS_2+Cu$, $LiF+Ni-Cr-Mo-Si$, and $LiF+Co-Mo-Cr-Si$. The content of solid lubricant is desirably 25~75 wt %.

In order to coat the mixture of the solid lubricant and the binder onto the slide surface of the metallic member, for instance, a flame spraying technique may be suitably used including a plasma spraying.

These and other objects, features and advantages of the invention will be appreciated upon reading of the following description of the invention when taken in conjunction with the attached drawing, with the understanding that some modifications, variations and changes of the same could be made by the skilled person in the art to which the invention pertains without departing from the spirit of the invention or the scope of the claims appended hereto.

BRIEF DESCRIPTION OF THE DRAWING

For a better understanding of the invention, reference is made to the attached drawings, wherein:

FIGS. 2 through 6 are schematic views of specific embodiments of the present invention, i.e., FIGS. 2, 3, 4, 5 and 6 being a tappet cam assembly, a rocker arm-cam assembly, a valve- valve seat assembly, a cylinder liner- piston ring assembly, and a rolling bearing, respectively.

DETAILED DESCRIPTION OF THE INVENTION

Figure 1:
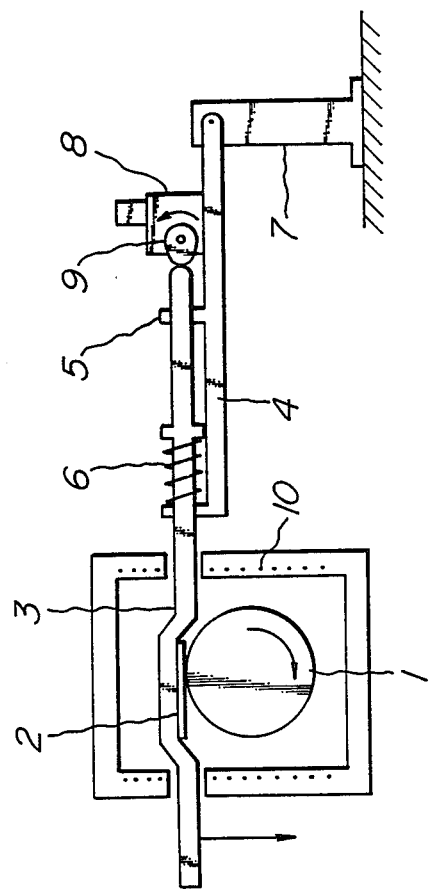
FIG. 1 is a schematic view of a testing apparatus used for measuring sliding performances of the slide assemblies according to the present invention.

Considering that a ceramic member must afford a low coefficient of friction and a wear amount must be small during sliding between the ceramic member and a metallic member coated with a solid lubricant and a binder, for instance, silicon nitride, sialon, mullite, partially stabilized zirconia or silicon carbide may preferably be used as a ceramic material constituting the ceramic member.

According to the present invention, the slide assemblies may include contact type slide assemblies such as valves and valve seats as well as rolling contact type slide assemblies such as rollers and bearings.

Further, the terms "coating and its derivatives" used herein may include a partial coating. Particularly, the coating may include coating of the mixture consisting of the metallic member and the binder on sliding an uneven surface of the metallic member in a scattered manner.

On the other hand, the term "solid lubricant" used herein means a substance which has a lubricating action in a solid state and includes LiF, PbO, an $MoS_2$. Further, the binder denotes a substance which can fix the solid lubricant onto the sliding surface of the metallic member including at least the sliding surface, and encompasses $MoO_3$, Cu, Ni—Cr—Mo—Si, and Co—Mo—Cr—Si.

The above-mentioned ceramic materials have high strength, thermal shock resistance, and high oxidation resistance, and possess preferable characteristics as slide members to be used in a high temperature dry atmosphere. In DE-OS Nos. P 2131509 and 2041282, a part of combinations of the solid lubricants and the binders disclosed herein are described as a sealing material at a sliding interface between a ceramic regenerator and a metallic member in a gas turbine. While the ceramic materials used as regenerators are required to have a low coefficient of thermal expansion, so high strength is not required. Thus, porous ceramic materials such as cordierite are generally used. In this respect, the above DE-OS publications differ from the present invention with respect to the object and kinds of the ceramic materials used.

The present invention is constituted as mentioned above, and is based on a novel discovery that when the ceramic member made of formerly known silicon nitride, sialon, partially stabilized zirconia, silicon carbide or the like is slided with a metallic member having a sliding surface coated with a mixture of a given solid lubricant and a given binder, coefficient of friction is low and a wear amount is small. As the metallic member, use may be made of any material used as a slide member so long as it is not contrary to the object of the present invention.

In the following, embodiments of the present invention will be explained with reference to the attached drawings.

FIG. 1 is a schematic view illustrating a testing apparatus used for measuring sliding performances such as wearing of slide assemblies according to the present invention. One of test pieces, a ceramic member, was set as a roller of 50 mm in a diameter in the testing apparatus. The ceramic roller 1 was rotated at 1,000 rpm by a drive unit not shown. On the other hand, a mating slide member 2 as the other test piece which was made of a high speed tool steel or the like was worked in a form of 40 mm×6.33 mm×3 mm, and was set at an arm 3, contacting the roller 1 as shown in FIG. 1. One end of the arm 3 was attached to a support member 4 via a bearing 5 and a spring 6. The support member 4 was designed to pivot at a pivot fixing member 7. Inside the support member 4, the tip of the arm 3 contacts a cam 9 which is connected to a drive unit 8 rotating at a speed of 3 rpm. The arm is moved back and forth three times per minute at a stroke of 12 mm by the cam in cooperation with the bearing 5 and the spring 6. A force of 20 N was downwardly applied to the other end of the arm 3 so that the ceramic roller 1 and the mating member 2 might be in contact with each other under a constant load. The ceramic roller 1 and mating member 2 were enclosed in a heating furnace 10 which allowed testing at high temperatures.

A frictional force during sliding was measured by a torque meter (not shown) which was attached to the shaft (not shown) around which was fitted the roller 1, and a coefficient of friction was determined based on the frictional force and the load. A change in the weight of the roller before and after the testing was measured by a balance at a precision of 0.0001 g. A change in the thickness of the mating member at the sliding portion before and after the testing was measured as the wear depth of the mating member at a precision of 1 μm by using a micrometer.

In the following, examples of the slide assemblies according to the present invention will be explained. These examples are merely in illustration of the invention, but should never be interpreted to limit the scope thereof.

EXAMPLE 1

By using the above-mentioned testing apparatus, sliding tests were effected between a roller of silicon nitride and a metallic member coated with a solid lubricant and a binder while kinds of the solid lubricant and the binder were varied. A high speed tool steel was used as the mating slide member, and recesses having an average diameter of 380 μm and the average depth of 75 μm were formed by etching on the entire surface of the mating slide member to be coated.

After the solid lubricant and the binder shown in Table 1 were coated onto the mating slide member by flame spraying, the coated layer was ground and polished to a thickness of 25 μm.

The sliding test was conducted at a temperature of 540° C. with dry condition. As a conventional example, a sliding test was conducted under the same conditions by using a mating slide member coated with Cu+LiF disclosed in Japanese patent application Laid-open No. 62-13,820. Results are shown in Table 1. In Table 1, positive values in "change in roller weight" denote that a lubricating layer was formed on the roller through the meal being transferred thereon and that a coefficient of friction was low. To the contrary, negative values denote that the roller was worn by an amount greater than the metal-transferred amount.

TABLE 1

| No. | Solid lubricant | Binder | Mixing ratio of solid lubricant/ binder | Wear depth in mating member (μm) | Change in roller weight (g) | Coefficient of friction |
| --- | --- | --- | --- | --- | --- | --- |
| Conventional Example | LiF | Cu | 50/50 | 110 | +0.002 | 0.38–0.42 |
| Present Invention | | | | | | |
| 2 | LiF | MoO$_3$ | 50/50 | 30 | +0.002 | 0.19–0.27 |
| 3 | PbO | Cu | 75/25 | 50 | +0.005 | 0.22–0.30 |
| 4 | PbO | Cu | 50/50 | 60 | +0.001 | 0.27–0.32 |
| 5 | MoS$_2$ | Cu | 50/50 | 90 | +0.000 | 0.20–0.27 |
| 6 | LiF | Ni-15 Cr-32 Mo-3Si | 50/50 | 80 | +0.000 | 0.22–0.28 |
| 7 | LiF | Co-28.5 Mo-17.5 Cr-3.4Si | 25/75 | 80 | +0.001 | 0.2–0.26 |
| Comparative Example | | | | | | |
| 8 | LiF | Ni | 50/50 | 190 | −0.001 | 0.35–0.46 |
| 9 | LiF | S316 | 50/50 | 340 | −0.001 | 0.42–0.50 |
| 10 | LiF | CoO | 50/50 | 190 | −0.004 | 0.38–0.52 |
| 11 | CaF$_2$ | Cu | 50/50 | 140 | −0.010 | 0.35–0.43 |

From the test results, it is seen that the slide assemblies according to the present invention had lower coefficients of friction and smaller wear amounts as compared with that comprising the metallic member coated with Cu+LiF. To the contrary, the slide assemblies outside the present invention showed higher coefficients of friction and greater wear amounts.

In general, when a metallic member is slided with a ceramic member with dry condition, the metal is transferred onto the ceramic member to form a lubricating layer on a sliding surface of the ceramic member. Thus, a coefficient of thermal friction becomes low. According to the present invention, low friction and less wearing are realized by a synergistic effect of a lubricating layer which is formed when the metal or the metal oxide used as the binder is transferred onto the ceramic member and the solid lubricant.

Example 2

By using a solid lubricant-binder combination of LiF+MoO₃ which showed excellent sliding performances in Example 1, sliding tests were conducted with respect to ceramic rollers made of silicon carbide, zirconia, sialon, and mullite under the same conditions as in Example 1.

Results are shown in Table 2.

TABLE 2

| No. | Roller material | Wear depth in M2 steel (μm) | Change in roller weight (g) | Coefficient of friction |
| --- | --- | --- | --- | --- |
| 101 | Silicon nitride | 30 | +0.002 | 0.19–0.27 |
| 102 | silicon carbide | 30 | +0.003 | 0.21–0.29 |
| 103 | Zirconia | 20 | +0.001 | 0.20–0.26 |
| 104 | Sialon | 30 | 0.000 | 0.22–0.31 |
| 105 | Mullite | 30 | +0.001 | 0.23–0.30 |

It is seen from Table 2 that every ceramic rollers tested exhibited equivalent coefficient of friction and wear amount and therefore the combinations of the solid lubricants and the binders according to the present invention are all effective to ceramic materials such as silicon nitride, silicon carbide, zirconia, sialon, mullite and the like.

FIGS. 2 through 6 show specific embodiments of the slide assemblies according to the present invention.

In FIG. 2, reference numerals 11, 12 and 13 are a metal cam, a coat of a solid lubricant and a binder upon the surface of the metal cam, and a ceramic tappet, respectively. In FIG. 3, reference numerals 14 and 17 are a metal cam and a rocker arm, respectively. A reference numeral 16 is a ceramic rocker arm tip applied to a cam-containing end portion of the rocker arm 15, and a reference numeral 17 is a coat of a mixture of a solid lubricant and a binder upon the surface of the metal cam. In FIG. 4, reference numerals 18 and 19 are a ceramic valve and a metal valve seat, respectively, and reference numeral 20 is a coat of a solid lubricant and a binder upon a valve-containing face of the valve seat. In FIG. 5, reference numerals 21 and 22 are a ceramic cylinder liner and a piston body, respectively, and reference numerals 23 and 24 are a metal piston ring and a coat of a solid lubricant and a binder upon the outer peripheral surface of the metal piston ring, respectively. In FIG. 6, reference numerals 25, 26, and 27 are a ceramic ball, a metal washer, and a metal cage, respectively. A reference numeral 28 is a coat of a solid lubricant and a binder upon a ball-contacting surface of each of the cage and the metal washer. Since the function and effects attained in the above embodiments according to the present invention are the same as or similar to those previously mentioned, explanation thereof is omitted.

As is clear from the foregoing explanation, according to the slide assemblies of the present invention, excellent wear-resisting and friction-resisting performances can be obtained even at high temperature with dry conditions in which engines (FIGS. 2~5) or high temperature bearings (FIG. 6), and the like are used, by coating the sliding surfaces of the metallic members with the mixture of the given solid lubricants and binders.

What is claimed is:

1. A slide assembly comprising a metallic member and a ceramic member, wherein at least a sliding surface of the metallic member which contacts said ceramic member is coated with a mixture consisting essentially of a solid lubricant and a binder, said mixture being a combination selected from the group consisting of LiF+MoO₃, PbO+Cu, LiF+Ni—Cr—Mo—Si, and LiF+Co—Mo—Cr—Si.

2. A slide assembly according to claim 1, wherein the slide assembly is an engine part.

3. A slide assembly according to claim 1, wherein the slide assembly is a combination selected from the group consisting of a tappet-cam assembly and a rocker arm-cam assembly.

4. A slide assembly according to claim 1, wherein the slide assembly is a valve-valve seat assembly.

5. A slide assembly according to claim 1, wherein the slide assembly is a linear-piston ring assembly.

6. A slide assembly according to claim 1, wherein the slide assembly is a rolling bearing.

7. A slide assembly according to claim 1, wherein said ceramic member comprises a ceramic material selected from the group consisting of silicon nitride, sialon, mullite, partially stabilized zirconia, and silicon carbide.

8. A slide assembly according to claim 7, wherein the slide assembly is an engine part.

9. A slide assembly according to claim 7, wherein the slide assembly is a combination selected from the group consisting of a tappet-cam assembly and a rocker arm-cam assembly.

10. A slide assembly according to claim 7, wherein the slide assembly is a valve-valve seat assembly.

11. A slide assembly according to claim 7, wherein the slide assembly is a liner-piston ring assembly.

12. A slide assembly according to claim 7, wherein the slide assembly is a rolling bearing.

13. A metallic slide member comprising a metallic base body and a layer of a mixture coated onto a sliding surface of the metallic base body, said mixture consisting essentially of a solid lubricant and a binder, said mixture being a combination selected from the group consisting of LiF+MoO₃, PbO+Cu, LiF+Ni—Cr—Mo—Si, and LiF+Co—Mo—Cr—Si.

* * * * *